(12) United States Patent
Kadomatsu et al.

(10) Patent No.: US 7,820,160 B2
(45) Date of Patent: *Oct. 26, 2010

(54) MIDKINE INHIBITORY COMPOSITIONS FOR THE TREATMENT OF ANGIOSTENOSIS

(75) Inventors: Kenji Kadomatsu, Aichi (JP); Mitsuru Horiba, Aichi (JP); Takashi Muramatsu, Aichi (JP); Shinya Ikematsu, Kanagawa (JP); Sadatoshi Sakuma, Kanagawa (JP)

(73) Assignee: Medical Therapies Limited, Sydney (AU)

( * ) Notice: Subject to any disclaimer, the term of this patent is extended or adjusted under 35 U.S.C. 154(b) by 161 days.

This patent is subject to a terminal disclaimer.

(21) Appl. No.: 11/936,438

(22) Filed: Nov. 7, 2007

(65) Prior Publication Data

US 2008/0107659 A1    May 8, 2008

Related U.S. Application Data

(60) Division of application No. 10/703,783, filed on Nov. 6, 2003, now Pat. No. 7,309,695, which is a continuation of application No. 09/763,586, filed as application No. PCT/JP99/04550 on Aug. 24, 1999, now abandoned.

(30) Foreign Application Priority Data

Aug. 24, 1998  (JP)  .............................. 10/251812

(51) Int. Cl.
*A61K 39/395* (2006.01)
*A61K 48/00* (2006.01)

(52) U.S. Cl. .............. 424/130.1; 424/135.1; 424/141.1; 424/142.1; 514/44 A; 536/23.1

(58) Field of Classification Search ........................ None
See application file for complete search history.

(56) References Cited

U.S. PATENT DOCUMENTS

| | | | |
|---|---|---|---|
| 5,521,004 | A | 5/1996 | Reiners et al. |
| 5,629,284 | A | 5/1997 | Unoki et al. |
| 5,670,477 | A | 9/1997 | Poduslo et al. |
| 5,733,871 | A | 3/1998 | Alps et al. |
| 5,994,524 | A | 11/1999 | Matsushima et al. |
| 6,024,956 | A | 2/2000 | Matsushima et al. |
| 6,048,972 | A | 4/2000 | Matsushima et al. |
| 6,068,840 | A | 5/2000 | Matsushima et al. |
| 6,083,907 | A | 7/2000 | Uchida et al. |
| 2003/0072739 | A1 | 4/2003 | Takada et al. |
| 2004/0219129 | A1 | 11/2004 | Yoshida et al. |

FOREIGN PATENT DOCUMENTS

| | | |
|---|---|---|
| JP | 07-009641 A | 4/1994 |
| JP | 8-27021 A | 1/1996 |
| JP | 8-73498 A | 3/1996 |
| WO | PCT/US95/08781 A | 2/1996 |
| WO | WO 99/34493 | 7/1998 |
| WO | WO 99/16463 A1 | 4/1999 |
| WO | WO 99/38971 A | 8/1999 |

OTHER PUBLICATIONS

Shoyab et al., Ampriregulin-associated protein: complete amion acid sequence of a protein produced by the 12-0-tetradecanoylphorbol-13-acetate-treated human breast adenocarcinoma cell line MCF-7, Biochem. Biophys. Res. Comm. 179(1):571, 1991 (abstract only).*
Agrawal, S. (1996) *Trends Biotechnol.* vol. 14, No. 10, pp. 376-387.
Berk, Bradford C. et al. (May 1991) "Pharmacologic Roles of Heparin and Glucocorticoids to Prevent Restenosis After Coronary Angioplasty" *J. Am. Coll Cardiol.* 17(6 Suppl B):111B-117B.
Braasch, D.A. (2002) *Biochemistry.* vol. 41, No. 14, pp. 4503-4510.
Branch, A.D. (1998) *Trends Biochem. Sci.* vol. 23, No. 2, pp. 45-50.
Griffith, M. (1997) "Midkine and Secondary Neurulation" *Teratology.* vol. 55, pp. 213-223.
Kojima et al. (Mar. 1996) "Human Ryudocan from Endothelim-like Cells Binds Basic Fibroblast Growth Factor, Midkine, and Tissue Factor Pathway Inhibitor." *The Journal of Biological Chemistry.* vol. 271, No. 10, pp. 5914-5920.
McCune, et al. Sep. 2001, J. Am. Med. Assoc. vol. 286, No. 10, pp. 1149-1152.
Muramatsu, H. et al. (1996) "Enzyme-Linked Immunoassay for Midkine, and Its Application to Evaluation of Midkine Levels in Developing Mouse Brain and Sera from Patients with Hepatocellular Carcinomas" *J. Biochem.* vol. 119, pp. 1171-1175.
Muramatsu, H. et al. (1993) *Developmental Biology.* vol. 159, pp. 392-402.
Ohyama, Y. et al. (1994) "Isolation and identification of midkine and pleiotrophin in bovine follicular fluid" *Mol. Cell Biol.* vol. 105, pp. 203-208.
Ratovitski et al. (1993) "Midkine induces tumor cell proliferation and binds to a high affinity signaling receptor associated with JAK tyrosine kinases" *The Journal of Biological Chemistry.* vol. 273, No. 6, pp. 3654-3660.
Sun, Xue-Zhi et al. (Dec. 1997) "An Immunohistochemical Study of Radial Glial Cells in the Mouse Brain Prenatally Exposed to γ-irradiation" *Journal of Neuropathology and Experimental Neurology.* vol. 56, No. 12, pp. 1339-1348.
Tamm, I. et al. (2001) *The Lancet.* vol. 358, pp. 489-497.
Wang, Sha-Yan et al. (1998) "Midkine exists in astrocytes in the early stage of cerebral infarction" *Developmental Brain Research* vol. 106, pp. 205-209.

(Continued)

*Primary Examiner*—Gary B. Nickol
*Assistant Examiner*—Claire Kaufman
(74) *Attorney, Agent, or Firm*—Morrison & Foerster LLP

(57) ABSTRACT

The present invention provides a pharmaceutical composition for the prevention or treatment of angiostenosis, comprising a compound inhibiting the function of midkine (MK) in blood vessel tissues as an effective ingredient. The present invention is useful for the prevention or treatment of angiostenosis attributed to arteriosclerosis or restenosis after percutaneous transluminal coronary angioplasty (PTCA). As compounds inhibiting the function of MK, antisense oligonucleotides that bind to a segment of a single-stranded mRNA transcribed from the MK gene to inhibit the synthesis of MK protein in cells, antibodies against the MK protein, and such can be used.

9 Claims, 5 Drawing Sheets

OTHER PUBLICATIONS

Rha, S.Y. et al. "Comparison of Biological Phenotypes According to Midkine Expression in Gastric Cancer Cells and Their Autocrine Activities Could be Modulated by Pentosan Polysulfate" *Cancer Letters*, 1997, pp. 37-46, vol. 118.

Yoshida, Y. et: al. "Midkine is present in the early stage of cerebral infarct", *Dev. Brain Res.*, 1995, 85:25-30.

Gewirtz, A.M. et al. "Facilitating oligonucleotide delivery: helping antisense deliver on its promise" *Proc. Natl. Acad. Sci.* 1996, vol. 93, pp. 3161-3163.

Green et al. "Antisense oligonucleotides: An evolving technology for the modulation of gene expression in human disease" *Antisense Therapy in Human Disease*, 2000, 191:93-105.

Jen et al. "Suppression of gene expression by targeted disruption of messenger RNA: Available options and current strategies" *Stem Cells*, 2000, 18:307-319.

Carmeliet et al. "Mouse models of angiogenesis, arterial stenosis, atherosclerosis and hemostatis" *Cardio. Res.*, 1998, 39:8-33.

Hayashi et al. "Antisense oligoribonucleotide as to the growth factor midkine suppresses neointima formation induced by balloon injury" *Am. J. Physiol. Heart Circ. Physiol.*, 2005, 288:H2203-H2209.

Bennet et al. "Antisense therapy for angioplasty restenosis" *Circulation*, 1995, 92:1981-1993.

Garas et al. "Overview of therapies for prevention of restenosis after coronary interventions" *Pharma. & Therap.*, 2001, 92:165-178.

Morishita et al. "Intimal hyperplasia after vascular injury is inhibited by antisense cdk 2 kinase oligonucleotides" *J. Clin. Invest.*, 1994, 93:1458-1464.

Horiba et al. "Midkine (MK) plays a crucial role in neointimal formation" *J. Amer. College Cardio.*, 1991, 33(2, Supp A):229A-230A.

Fazekas et al., Journal of Immunological Methods (1980) 35:1-21.

Galfre et al., Nature (1979) 277:131-133.

Galfre et al., Methods in Enzymology (1981) 73:3-46.

Giovannangeli et al., PNAS USA (1993) 90:10013-10017.

Haeuptle et al., Nucleic Acids Research (1986) 14(3):1427-1448.

Kadomatsu et al., Biochemical and Biophysical Research Communications (1988) 151(3):1312-1318.

Kaneda et al., J. Biochem. (1996) 119:1150-1156.

Kearney et al., J. Immunology (1979) 123(4):1548-1550.

Kohler and Milstein, Eur. J. Immunol. (1976) 6:511-519.

Kohler and Milstein, Nature (1975) 256:495-497.

Kojima et al., JBC (1996) 271(10):5914-5920.

Kumar et al., Arteriosclerosis, Thrombosis, and Vascular Biology (1997) 17:2238-2244.

Kumar et al., Circulation (1997) 96:4333-4342.

Kuo et al., JBC (1990) 265(31):18749-18752.

Li et al., Science (1990) 250(4988):1690-1694.

Maeda et al., JBC (1996) 271(35):21446-21452.

Margulies et al., Cell (1976) 8:405-415.

Mercator Study Group, Circulation (1992) 86:100-110.

Muramatsu, Develop. Growth & Differ. (1994) 36:1-8.

Nakamura et al., Genes to Cells (1988) 3:811-822.

Nobuyoshi et al., JACC (1991) 17(2):433-439.

Parker, Experimental Atherosclerosis (1960) 36:19-53.

Rauvala, The EMBO Journal (1989) 8(10):2933-2941.

Ross, New England Journal of Medicine (1986) 314(8):488-500.

Ross, Nature (1993) 362:800-809.

Schwartz et al., Circulation Research (1995) 77:445-465.

Shulman et al., Nature (1978) 276:269-270.

Stein et al., Cancer Research (1988) 48:2659-2668.

Stein et al., Science (1993) 261:1004-1012.

Tomomura et al., JBC (1990) 265(18):10765-10770.

Trowbridge, J. Exp. Med. (1978) Jul. 1:313-323.

Tsutsui et al., Biochemical and Biophysical Research Communications (1991) 176(2):792-797.

Walder et al., PNAS USA (1988) 85:5011-5015.

Webster et al., American Journal of Pathology (1974) 76(2):245-264.

Weintraub et al., New England Journal of Medicine (1994) 331:1331-1337.

Wellstein et al., JBC (1992) 267(4):2582-2587.

Yelton et al., Curr. Top. Microbiol. Immunol. (1978) 81:1-7.

* cited by examiner (a) MK

C  3h  3d  7d  14d (b) HB-GAM

C  3h  3d  7d  14d (c)

Syndecan-1    Syndecan-3    Syndecan-4

C  3h  3d  7d  14d    C  3h  3d  7d  14d    C  3h  3d  7d  14d (d) RPTP-β

C  3h  3d  7d  14d (e) GAPDH

C  -3h  3d  7d  14d

Competitive PCR

SEQUENCE LISTING

<160> NUMBER OF SEQ ID NOS: 15

<210> SEQ ID NO 1
<211> LENGTH: 30
<212> TYPE: DNA

```
<213> ORGANISM: Artificial Sequence
<220> FEATURE:
<223> OTHER INFORMATION: Artificially Synthesized Primer Sequence

<400> SEQUENCE: 1
gccggatcca tgcagcaccg aggcttcttc                                    30

<210> SEQ ID NO 2
<211> LENGTH: 42
<212> TYPE: DNA
<213> ORGANISM: Artificial Sequence
<220> FEATURE:
<223> OTHER INFORMATION: Artificially Synthesized Primer Sequence

<400> SEQUENCE: 2
actagcataa tcaggaacat catagtcctt tccttttcct tt                      42

<210> SEQ ID NO 3
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 3
actggtgccg agtgcaaaca a                                             21

<210> SEQ ID NO 4
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 4
gagtttgcca cagggcttgg a                                             21

<210> SEQ ID NO 5
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 5
ggaggcactt ctgtcatcaa                                               20

<210> SEQ ID NO 6
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 6
agcacttcct tcctgtccaa                                               20

<210> SEQ ID NO 7
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 7
gatgagccag aggtgccagt                                               20
```

```
<210> SEQ ID NO 8
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 8
gccacctacg atcacagcta                                                   20

<210> SEQ ID NO 9
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 9
gaagacgctg ggggccttga g                                                 21

<210> SEQ ID NO 10
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 10
tctgagggga cacggatgcc a                                                 21

<210> SEQ ID NO 11
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 11
atcggatccc cgttctcaac acatccctga at                                     32

<210> SEQ ID NO 12
<211> LENGTH: 33
<212> TYPE: DNA
<213> ORGANISM: Artificial Sequence
<220> FEATURE:
<223> OTHER INFORMATION: Artificially Synthesized Primer Sequence

<400> SEQUENCE: 12
cgtctcgagc taagcatctg gagaaaatgt ctc                                    33

<210> SEQ ID NO 13
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 13
gaccacagtc catgccatca c                                                 21

<210> SEQ ID NO 14
<211> LENGTH: 23
<212> TYPE: DNA
<213> ORGANISM: Artificial Sequence
<220> FEATURE:
```

-continued

```
<223> OTHER INFORMATION: Artificially Synthesized Primer Sequence

<400> SEQUENCE: 14
gtagccgtat tcattgtcat acc                                              23

<210> SEQ ID NO 15
<211> LENGTH: 728
<212> TYPE: DNA
<213> ORGANISM: Mus musculus

<400> SEQUENCE: 15
caggccggag cgggagggag cgaagcatcg agcagtgagc gagatgcagc accgaggctt      60
cttccttctc gcccttcttg ccctcttggt ggtcacgtcc gcggtggcca aaaaaaaga      120 gaaggtgaag aagggcagcg agtgttcgga gtggacctgg gggccctgca cccccagcag     180
caaggactgc ggcatgggct tccgcgaggg tacctgtggg gcccagaccc agcgcgtcca     240
ttgcaaggtg ccctgcaact ggaagaagga atttggagcc gactgcaaat acaagtttga     300
gagctggggg gcgtgtgatg ggagcactgg caccaaagcc cgccaaggga ccctgaagaa     360
ggcgcggtac aatgcccagt gccaggagac catccgcgtg actaagccct gcacctccaa     420
gaccaagtca aagaccaaag ccaagaaagg aaaaggaaag gactaagtca ggaggccaga     480
gagcctccgg cctcgcctgg agcctgaacg gagccctcct ctcccacagg cccaagatat     540
aacccaccag tgccttttgt cttcctgtca gctctgtcaa tcacgcctgt cctctcacgc     600
ccacaccaag tgcccaaagt ggggagggac aagagattct ggaaagtgag cctccccata     660
ccctcttttg ttctccccac cctgatactt gttattaaga aatgaataaa ataaactcac     720
tttttttcc                                                             728
```

MIDKINE INHIBITORY COMPOSITIONS FOR THE TREATMENT OF ANGIOSTENOSIS

CROSS-REFERENCE TO RELATED APPLICATIONS

The present application is a divisional of U.S. application Ser. No. 10/703,783, filed Nov. 6, 2003, now issued as U.S. Pat. No. 7,309,695, which is a continuation of U.S. application Ser. No. 09/763,586 filed Feb. 22, 2001, now abandoned, which is the National stage of International Application Number PCT/JP99/04550, filed Aug. 24, 1999, which claims priority to Japanese Patent Application No. JP 10/251,812, filed Aug. 24, 1998, each of which is hereby incorporated by reference herein in its entirety, including any figures, tables, nucleic acid sequences, amino acid sequences, and drawings.

TECHNICAL FIELD

The present invention relates to pharmaceutical compositions for the prevention and treatment of disorders attributed to intimal thickening, more specifically to pharmaceutical compositions for the prevention and treatment of these diseases, comprising MK or its inhibitor as an effective ingredient.

BACKGROUND ART

Incidence of ischemic cardiac diseases caused by arteriosclerosis, especially, coronary arteriosclerosis, such as angina pectoris, and myocardial infarction are recently on the increase. Pathological tissue images of arteriosclerosis mainly show local intimal thickening and diminished elasticity. As a result, circulation is disturbed, and nutrients and oxygen are insufficiently supplied to myocardial tissues, leading to the above-mentioned conditions.

Many important findings have been made regarding the pathogenesis of intimal thickening. A typical example is that the thickened intima primarily constitutes of smooth muscle cells that migrated from tunica media (Parker, F., Amer. J. Pathol., 1960, 36, 19-53; and Webster, W. S., S. P. Bishop & J. C. Geer, Amer. J. Pathol., 1974, 76, 245-264). Moreover, the hypothesis that arteriosclerosis develops as a result of the injury-repairing reaction (Ross, R., N. Engl. J. Med., 1986, 314, 488-500) is the base of understanding on arteriosclerosis even now.

Percutaneous transluminal coronary angioplasty (PTCA), a treatment in which a blood vessel constricted by such an intimal thickening is inflated by a balloon and physically expanded, is a common treatment at present. PTCA surgery has proved to be remarkably effective with a 90% or higher recovery rate. However, restenosis occurs with a frequency of 30 to 60% at the same site within 6 months or less following PTCA. It is pathologically recognized that restenosis is the result of an excessive repairing mechanism, the excessive neointima formation at the artery wall of the injured site (Nobuyoshi, M. et al: J. Am. Coll. Cardiol. 17: 433-439, 1991). It has also been confirmed that this neointima forms from tunica media-derived smooth muscle cell migration and proliferation, and hyperplasia of the extracellular matrix. The following molecular biological mechanism in the neointima formation process is known. First, a transformation of blood vessel smooth muscle cells from a contractile to a synthetic phenotype is observed. Further, the following substances that induce cell proliferation, and overexpression of their receptors, have been reported:

various growth factors, such as platelet-derived growth factor (PDGF) and Fibroblast growth factor (FGF);
cytokines, such as interleukin and tumor necrosis factor α (TNFα);
Angiotensin II; and
Thrombin.

Based on these backgrounds, it could be hypothesized that restenosis can be prevented by inhibiting the migration and proliferation of blood vessel smooth muscle cells. Thus, many pharmaceuticals were examined for their inhibitory effects on intimal proliferation using animal experiments. Effective ones were clinically tested, however, no effectiveness could be clinically established for any of these pharmaceuticals (Circulation., 1992, 86, 100-110; and Weint raub, W. S. et al., N. Engl. J. Med., 1994, 331, 1331-1337).

Midkine (MK) was discovered as a gene product, expression of which is induced at the early stage of the differentiation induction process of embryonic tumor cells by retinoic acid (Kadomatsu, K. et al., Biochem. Biophys. Res. Commun., 1998, 151, 1312-1318). Pleiotrophin (PTN, or HB-GAM) was discovered as a binding protein having neurite elongation ability in the brains of newborn rats (Rauvala, H., 1989, EMBO J., 8, 2933-2941). MK and PTN are heparin-binding proteins which control cell proliferation, survival, and differentiation in the developmental process (Tomomura, M. et al., J. Biol. Chem., 1990, 265, 10765-10770; Li, Y. et al., Science, 1990, 250, 1690-1694; Rauvala, H., EMBO J., 1989, 8, 2933-2941; Wellstein, A. et al., J. Biol. Chem., 1992, 267, 2582-2587), have about a 50% sequence homology (Tomomura, M. et al., J. Biol. Chem., 1990, 265, 10765-10770; Kuo, M. et al., J. Biol. Chem., 1990, 265: 18749-18752; and Tsutsui, J. et al., Biochem. Biophys. Res. Commun., 1991, 176, 792-797), and form the MK family (Muramatsu, T., Dev. Growth Differ., 1994, 36, 1-8).

A mature MK protein is a protein with a molecular weight of 13,000, comprising 121 amino acids rich in basic amino acids and cysteins. Its function is various, including, for example, promoting survival of nerve cells, neurite elongation, accelerating fibrinolysis in endothelial cells of blood vessels, and transformation of NIH3T3 cells. In addition to these, involvement of MK in tissue reconstitution has been recently drawing attention. Expression of MK was observed in gliocytes around brain infarction nidi, mainly in the epithelial side of the region where interaction between the epithelium and stroma takes place during development, etc.

However, no relationship between arteriosclerosis and restenosis after PTCA and MK protein has been reported.

DISCLOSURE OF THE INVENTION

An objective of the present invention is to provide a novel drug for controlling neointima formation, especially to provide a novel drug effective for the treatment of arteriosclerosis and prevention of restenosis following PTCA surgery.

The present inventors revealed a role for MK in neointima formation based on the following understandings. The results of RT-PCR and competitive PCR conducted on mRNA prepared from the blood vessel tissue of rat common carotid artery endothelium-injury model confirmed that the expression of MK mRNA was increased in the period from 7 to 10 days after injury. The neointima in the wild mice was remarkably enlarged compared with that in MK knockout mice in the neointima formation models prepared from the wild and MK knockout mice. Further, the injection of MK increased neointima size in MK knockout mice.

Based on these findings, the present inventors proposed that MK has an important role in intimal thickening. The present invention revealed that inhibiting the function of MK in cells represses the corresponding proliferation-stimulatory activity, in which MK was involved, to prevent arteriosclerosis and restenosis after PTCA surgery, and completed the invention.

Specifically, the present invention relates to the following pharmaceutical composition and a method for screening compounds for the pharmaceutical composition, namely to:

(1) a pharmaceutical composition for the prevention or treatment of angiostenosis, comprising a compound inhibiting the functions of MK as an effective ingredient;

(2) the pharmaceutical composition of (1), wherein the compound inhibiting the function of MK is an antisense oligonucleotide that inhibits intracellular MK protein synthesis by binding to a segment of a single-stranded mRNA transcribed from the MK gene;

(3) the pharmaceutical composition of (1), wherein the compound inhibiting the function of MK is an antibody against the MK protein or a fragment comprising its variable region;

(4) the pharmaceutical composition of (1), wherein angiostenosis is caused by arteriosclerosis or restenosis after PTCA surgery;

(5) a method for screening a compound for the prevention or treatment of angiostenosis, comprising the steps of:

(a) contacting MK expressing cells with a candidate compound; and, (b) selecting a compound inhibiting the function of MK; and, (6) a pharmaceutical composition for the prevention or treatment of angiostenosis, comprising a compound selected by the method of (5) as an effective ingredient.

The present invention provides a pharmaceutical composition for the prevention or treatment of restenosis, comprising a compound inhibiting the function of MK as an effective ingredient. Alternatively, the present invention relates to the use of the compound inhibiting the function of MK in the prevention or treatment of restenosis. Moreover, the present invention relates to the use of a compound inhibiting the function of MK in the production of a pharmaceutical composition for the prevention or treatment of restenosis.

In the present invention, the function of MK includes a whole series of steps in which the MK gene is transcribed, translated into proteins, and its activity is expressed. Therefore, inhibiting the function of MK is meant by the inhibition of any step comprising this series of processes. Specifically, usable compounds in the present invention include, for example, antisense nucleic acids or decoy nucleic acids of the MK gene, which inhibit the transcription of the gene and translation into proteins, ribozymes which damage mRNA encoding MK, and MK protein-binding compounds that interfere with the activity expression of MK proteins.

The present inventors examined the expression of MK, HB-GAM (Heparin-binding Growth-associated Molecule; Pleiotrophin), Syndecan family (Syndecan-1, Syndecan-3, and Syndecan-4), RPTP-β (one of receptors of PTN), and glyceraldehyde phosphate dehydrogenase (GAPDH; a housekeeping gene) (internal standard), using mRNA prepared from blood vessel tissues in the rat carotid artery endothelium-injury model through RT-PCR. As a result, MK mRNA expression was increased in the period of 7 to 14 days after injury (FIG. 1a). In Syndecan-1, a strong mRNA expression was observed in the period of 3 to 14 days after injury, synchronizing with the expression pattern of MK. Syndecan-1 is a member of the Syndecan family, and is considered to work as a receptor for MK.

On the other hand, the expression of PTN, a member of the MK family, was temporally increased at about 7 days after injury. RPTP-β, considered as a receptor of PTN (J. Biol. Chem. 271, 21446-21452, 1996), showed strong mRNA expression in the period of 3 to 7 days after the operation, in which period the expression of HB-GAM expression was expected to be elevated and at peak-level. GAPDH used as the internal standard showed a constant expression regardless of the number of days following the operation (FIG. 1e).

Competitive PCR confirmed that GAPDH constantly showed the same level of expression until 14 days after the operation ($10^5$ copies/μl) while the expression of MK was increased ten-fold at day 7 following the operation (FIG. 2). Therefore, MK is expressed in such a manner that mRNA expression reaches maximum at 7 days after the operation. Western-blotting analysis in each tissue at 3 days, 7 days, and 14 days after the operation indeed showed the MK protein, clearly showing a large amount of expression at 7 days after the operation (FIG. 2). From the above results, MK was seen to have an mRNA expression pattern different from PTN, which is a member of the MK family, and only MK is considered to be expressed in harmony with neointima formation.

Blood vessel tissues obtained from rats at 14 days after the operation were stained with hematoxyline-eosin to examine the formation of neointima following endothelial injury (Circulation, 1997, 96, 4333-4342). The intima was not formed while the tunica media following the adventitia was enlarged, confirming the growth of blood vessel smooth muscle (FIGS. 4b and c). In contrast, the intima of the untreated rat was made of well-formed adventitia, media, and intima (FIG. 4a). Immunohistochemical staining by anti-MK antibody (Japanese Patent Application No. Hei 9-205332) showed stained proliferating blood vessel smooth muscle cells in the blood vessel tissues from rats at 14 days following the operation (FIG. 4d). These results confirmed that MK is involved in the proliferation of smooth muscle cells. Therefore, restenosis after PTCA surgery would be preventable by inhibiting MK function. Since a mechanism similar to angiostenosis after PTCA surgery presumably functions in arteriosclerosis nidi as well (Nature, 1993, 362, 801-809; and Circulation, Res., 1995, 77, 445-465), arteriosclerosis would also be preventable and treatable by inhibiting MK function.

Inhibition of MK function can be achieved by, for example, inhibiting the synthesis of the MK protein itself. This is done by repressing the transcription, expression, or translation of the MK gene. For this purpose, for example, antisense nucleic acids or decoy nucleic acids can be used. In antisense nucleic acid techniques, a gene comprising a nucleic acid sequence hybridizing with the desired gene, or an artificially synthesized short nucleic acid chain (antisense-oligo) is introduced to repress the expression of a specific gene using the complementarity of genes. In contrast, decoy nucleic acid pharmaceuticals inhibit the binding of a specific transcriptional regulatory factor to its binding site, repressing an activated gene group.

The antisense technique provides an extremely specific and powerful method for inhibiting gene products (Stein & Chang, Science, 1993, 261, 1004-1012). By hybridizing an antisense oligonucleotide with an mRNA target, the expression of the corresponding gene product can be inhibited through multiple mechanisms. In the "translation arrest" state, the activity of a ribosome complex can be repressed by the interaction between a target mRNA and an oligonucleotide to prevent translation from mRNA to a protein (Haeuptle et al., Nucl. Acids. Res. 14, 1986, 1427). In the case of phosphodiester DNA or phosphorothioate DNA oligonucleotides, when a sequence of a target RNA hybridizes with its DNA oligomer, intracellular RNase H can quickly digest its target RNA sequence (Walder & Walder, Proc. Natl. Acad. Sci. USA., 1988, 85, 5011). Some kinds of oligonucleotides can form a "triplex," that is a triple-helix structure, with standard double-stranded genomic DNA containing a target gene to prevent transcription by RNA polymerase (Giovannangeli et al., Proc. Natl. Acad. Sci. USA., 1993, 90, 10013).

A typical antisense oligonucleotide is a short DNA sequence normally comprising 10 to 50 bases and complementary to a specific region of the corresponding target mRNA. Hybridization of a target transcript with an antisense oligonucleotide forms complementary base pairs, and therefore, shows a high specificity. Hybridization of the antisense oligonucleotide is affected by the accessibility of the antisense oligonucleotide to the target site, chemical modification, secondary structure (Stein et al., Cancer Research, 1988, 48, 2659), etc.

In order to select the desired length of an antisense oligonucleotide against mRNA the expression of which should be repressed, the following factors must be considered. First, such a short oligonucleotide comprising 10 to 15 bases shows high cellular invasiveness, while its gene specificity is low. In contrast, a long oligonucleotide made of 20 to 30 bases shows a high specificity, while the cell incorporation rate is low. The ability of accessing an mRNA target sequence is also important. For example, a loop forming region existing in a target mRNA can easily have access to an antisense oligonucleotide because of the high probability of existing as a single strand, and therefore, has potential to be a target nucleotide sequence. It should be obvious to one skilled in the art to select an appropriate target sequence and length of an antisense oligonucleotide by considering these factors.

The term "oligonucleotide" used herein includes both nucleic acid parts of oligomers existing in nature, such as the structures of deoxyribonucleotides in DNA and ribonucleotides in RNA, and artificial analogues capable of binding to nucleic acids existing in nature. The oligonucleotide of this invention may be any oligonucleotide based on ribonucleotide monomer bound through a phosphodiester bond or through analogues bound through methylphosphonate, phosphorothioate, or other bonds. In these, the basic structures or other modifications are changed, although the monomer portion still retains the ability to bind to DNA and RNA structures existing in nature. These oligonucleotides can be prepared by a method well known to a person skilled in the art, for example, a method using a commercially available machine and reagents available from Perkin-Elmer Applied Biosystem (Foster City, Calif.). These apparatus can synthesize an oligonucleotide of about 100 bases, in nano moles.

An oligonucleotide bound through a phosphodiester bond is especially vulnerable to nucleases in blood or cells. Therefore, in the preferable embodiment, oligonucleotides used in this invention are analogues bound through a phosphorothioate bond or a methylophosphonate bond, which have been confirmed to be nuclease resistant (Stein et al., Cancer Research, 1988, 48, 2659).

MK oligonucleotides in the form of antisense RNA can be temporally expressed in target cells through a standard DNA expression vector. The MK DNA sequence can be cloned from a standard plasmid to an expression vector, and the expression vector has the property of expressing an endogenous oligonucleotide at a higher level or more effectively. At minimum, these constructs require a eukaryotic promoter sequence for initiating transcription of the inserted DNA sequence. A preferable expression vector can induce a high level of expression. This can be achieved by adding a control element that can increase the transcription of the downstream sequence within an appropriate host cell.

For example, the MK antisense oligo expression vector can be constructed through PCR by which an appropriate fragment obtained from a single-stranded cDNA of plasmid pHIL301-MK is amplified. An appropriate nucleotide sequence of an oligonucleotide primer for the PCR reaction can be designed based on the cDNA sequence of MK (GenBank Acc. No. J05447) by a person skilled in the art. The methods for synthesizing and purifying oligonucleotides are well known. A PCR product is subcloned into plasmids. In relation to this, a "cloning vector" is a DNA molecule, such as a plasmid, a cosmid, or bacteriophage, which can self-replicate in prokaryotic host cells. A cloning vector generally has not only a marker gene appropriate for identifying and selecting cells transformed by this cloning vector, but also one or a few restriction endonuclease recognition sites into which an exogenous DNA sequence can be inserted in a detectable manner without loosing the biological function essential for the vector. Marker genes include the tetracycline resistant gene and the ampicillin resistant gene. The cloned antisense fragment can be amplified by transforming an appropriate bacterial cell using the cloning vector, and proliferating the bacterial host cells in the presence of an appropriate antibiotic. Subsequently, PCR is conducted for the bacterial host cells, and clones having MK in an antisense orientation are screened.

The cloned antisense fragments can be cut out from the cloning vector and inserted into an expression vector. An appropriate expression vector generally includes (1) a prokaryotic DNA factor which encodes an origin of replication in bacterial hosts and an antibiotics resistant marker, (2) a factor for regulating the initiation of transcription such as a promoter, and (3) a DNA factor for regulating transcriptional processes such as a transcription termination/polyadenylation sequence. In mammalian hosts, transcriptional regulation and translational regulation signals are preferably derived from viruses, for example, adenoviruses, bovine papilloma viruses, or similar viruses. In these viruses, a regulatory signal is involved in specific genes leading to a high level of expression. An appropriate transcriptional regulatory sequence and translational regulatory sequence can also be obtained from mammalian genes, for example, the genes of actin, collagen, myosin, and methallothionine. A transcriptional regulatory sequence contains a promoter region that can appropriately initiate RNA synthesis. Preferable eukaryotic promoters include the mouse methallothionine 1 gene promoter, TK promoter of herpesvirus, Rous sarcoma virus promoter, and cytomegalovirus promoter.

Prokaryotic promoters, such as the bacteriophage T3RNA polymerase promoter, can be used to regulate expression of fused genes, as long as the prokaryotic cell promoter is regulated by a eukaryotic cell promoter.

An appropriate vector for expression in mammalian cells is a vector that provides a high level of transcription from the mammalian enhancer promoter sequence. The cloned MK antisense vector can be amplified within bacterial host cells, isolated from the cells, and analyzed as described previously.

Another possible method for using an antisense sequence is gene therapy. A virus-like vector generally derived from a retrovirus will prove to be useful as a carrier for the incorporation of antisense constitutes into the thickened tissues of blood vessels or the intima, and their expression. In general, the vector is not replicable in vivo, and therefore undesired infection to non-targeted cells can be prevented. In this case, the lack of replication ability is compensated in vitro providing a helper cell line capable of amplifying and enveloping antisense vectors.

The antisense oligonucleotides of this invention can be derived from any part of the open reading frame of MK cDNA. An mRNA sequence that preferably (1) exists around the translation initiation site and (2) forms a loop structure, is targeted. Statistical analysis based on the size of the human genome revealed that DNA segments consisting of about 14 to 15 base pairs have a specific sequence within the genome. In order to assure the specificity of the target sequence in MK RNA, the desirable length of the antisense oligonucleotide is at least 14 bases, more preferably, 15 bases. The oligonucleotides designed by the present invention include, for example, nucleotides corresponding to 1 to 14, 1 to 15, 1 to 16, 1 to 17, 1 to 18, 1 to 19, 2 to 16, 3 to 17 positions of MK cDNA sequence.

As a compound inhibiting the function of MK in the present invention, a compound that binds to the MK protein to interfere with the expression of its activity can be used. These compounds include the MK neutralizing antibody, heparin (refer to Kaneda, N. et al., j. Biochem. 1996, 119, 1150-1156), or Human ryudocan that inhibits activity by depriving the binding site of MK (refer to Kojima, T., Katsumi, A., Yamazaki, T., Muramatsu, T., Nagasaka, T., Ohsumi, K., and Saito, H., J. Biol. Chem., 1996, 271(10), 5914-5920).

The anti-MK protein antibody used in this invention can be obtained as a polyclonal or monoclonal antibody using well-known methods. As the anti-MK protein antibody used in this invention, a monoclonal antibody is preferable. The monoclonal antibody can be prepared by following a well-known method. For example, cDNA of human MK has been cloned and its DNA sequence and the encoding amino acid sequence have been reported. A monoclonal antibody can be prepared against the whole or part of the MK protein antigen. An antibody prepared against a soluble human MK protein antigen is most preferable.

A hybridoma producing the monoclonal antibody can be prepared basically by following the method of Kohler and Milstein (Kohler, G. & C. Milstein, Nature, 1975, 256, 495-497) as described below. The MK protein is used as a sensitizing antigen and immunized by standard immunization methods. The obtained immunized cells are fused with well-known mother cells by standard cell fusion methods. The monoclonal antibody producing cells can be screened by standard screening methods.

The MK protein used as a sensitizing antigen for obtaining the antibody can be prepared using, for example, MK gene/amino acid sequence described in unexamined published Japanese patent application (JP-A) No. Hei 9-95454 for human MK.

The number of amino acid residues in MK can be any, as long as MK is used as the antigen for obtaining the anti-MK antibody used in this invention. After the MK gene sequence is inserted in to a well-known expression vector system, and the appropriate host cells are transformed, target MK proteins are purified from the host cells or the culture supernatant using a known method, and the purified MK proteins are used as the sensitizing antigen. Mammals immunized by the sensitizing antigen are not particularly limited, however, it is preferable to select by considering the adaptability to the mother cells used for cell fusion. In general, rodents such as mice, rats, hamsters and such are used.

Animals are immunized with MK by a well-known method. For example, the general method is intraperitoneal or subcutaneous injection of MK into mammals. Specifically, MK diluted with PBS, physiological saline, and such to an appropriate concentration is suspended and, if necessary, mixed with an appropriate amount of a standard adjuvant, for example, Freund complete adjuvant, and after emulsification, administered to mammals several times every 4 to 21 days. An appropriate carrier can be used for immunization. After the desired antibody level is confirmed to be elevated in serum, immunized cells are taken from the mammals for cell fusion. A spleen cell is specifically desired as an immunized cell.

Preferable mammalian myeloma cells used as mother cells fused with the above-mentioned immunized cells, include various well-known cell lines, such as, P3 (P3x63Ag8.653) (Kearny, J. F. et al., J. Immunol., 1979, 123, 1548-1550), P3x63Ag8U.1 (Yelton, D. E. et al., Current Topics in Microbiology, 1978, 81, 1-7), NS-1 (Kohler, G. & Milstein, C. Eur. J. Immunol., 1976, 6, 511-519), MPC-11 (Margulies, D. H. et al., Cell, 1976, 8, 405-415), SP2/0 (Shulman, M. et al., Nature, 1978, 276, 269-270), F0 (de St. Growth, S. F. & Scheidegger, D. J. Immunol. Methods, 1980, 351-21), S194 (Trowbridge, I. S. J. Exp. Med., 1978, 148, 313-323), R210 (Galfre, G. et al. Nature, 1979, 277, 131-133), and such, are preferable.

The above-mentioned immunized cells and myeloma cells can be fused basically by following a well-known method, for example, the method of Milstein et al. (Galfre, G. & Milstein, C., Methods Enzymol. 73: 3-46, 1981). Specifically, the above-mentioned cell fusion can be performed, for example, in a standard nutrient culture medium in the presence of a cell fusion activator. As a cell fusion activator, for example, polyethylene glycol (PEG), and Sendai virus can be used. In order to enhance fusing efficiency, an adjuvant, such as dimethylsulfoxide, can be added.

The preferable ratio of immunized cells to myeloma cells is, for example, from 1 to 10 folds. As the culture medium for cell fusion, for example, RPMI 1640 culture medium and culture medium are suitable for myeloma cell lines, and other standard media used for this kind of cell culture can also be used. Further, a serum supplementary solution, such as fetal calf serum can be used in conjunction.

A desired hybridoma can be prepared by thoroughly mixing given amounts of immunized cells and myeloma cells in the above-mentioned culture medium, and mixing with a PEG solution, such as a PEG solution of an average molecular weight of about 1000 to 6000 that is pre-heated to about 37° C. and is usually added at the concentration of 30 to 60 percent (w/v). Subsequently, an appropriate culture medium is added thereto, and centrifuged to remove the supernatant. These steps are repeated to remove cell fusing agents, and such that are undesirable for hybridoma growth.

The hybridoma can be selected by culturing in a standard selection medium, such as the HAT culture medium. The culture in the HAT medium is continued long enough for the cells except the target hybridoma (non-fused cells) to die, normally for several days to several weeks. The standard limiting dilution is then applied to conduct screening and monocloning of the hybridoma producing the objective antibody.

In this invention, recombinant antibodies and modified antibodies can also be used. As a recombinant antibody, for example, one that is produced by using genetic engineering techniques, by cloning the antibody gene of a monoclonal antibody from hybridoma, inserting this into an appropriate vector, and introducing into a host cell (for example, Borrebaeck, C. A. K. & Larrick, J. W., Therapeutic Monoclonal Antibodies, Macmillan Publishers Ltd., United Kingdom, 1990). As a modified antibody, for example, a chimera antibody and a humanized antibody, can be used. A chimera antibody can be obtained by linking DNA which encodes the antibody V region other than that for the human antibody with a DNA encoding the human antibody C region, inserting it into an expression vector, and introducing into a host for production (EP 125023, PCT WO96/02576).

The antibody used in the present invention can be an antibody fragment or a modified antibody, as long as it binds to MK to inhibit its activity. An antibody fragment is, for example, Fab, F(ab')$_2$, Fv, or single chain Fv (scFv) in which H chain is linked to Fv of L chain with an appropriate linker.

In the present invention, the anti-MK antibody is used for inhibiting the function of MK by following the general antibody treatment (for example, intravenous infusion).

A pharmaceutical composition of the invention that comprises a compound inhibiting MK function as an effective ingredient, is formulated by well-known pharmaceutical preparation methods and administered to patients for the purpose of preventing or treating disorders attributed to intimal thickening, etc. The effective ingredient of the invention can be combined with an appropriate carrier or medium generally used for a pharmaceutical agent, for example, sterilized water, physiological saline, plant oil (for example, sesame oil, olive oil, etc.), coloring agents, emulsifiers (for example, cholesterol), suspending agents (for example, gum arabic), surfactants (for example, polyoxyethylene hydrogenated castor oil system surfactant), solubilizers, (for example, sodium phosphate), stabilizers (for example, sugar, sugar alcohol, albumin), preservatives (paraben) and such to prepare a formulation suitable for effective administration into the body, such as an injection, nasally absorbed agent, percutaneously absorbed agent, oral agent, and such, preferably an injection. A pharmaceutical agent for injection can be provided in a form such as a lyophilized form, an aqueous form, or in a form in which the pharmaceutical agent is filled into an osmotic pressure pump.

An injection can be obtained by dissolving the compound that is the effective ingredient, together with an appropriate dispersant, by dissolving or dispersing in a dispersion medium. Either an aqueous form or an oily form can be prepared by suitably selecting the dispersion medium. For an aqueous form, distilled water, physiological saline, Ringer's solution, and such can be used as the dispersion medium. For an oily form, various plant oils, propylene glycol, and such can be used. Preservatives, such as paraben, and such, can be added if necessary. A well-known isotonic agent, such as sodium chloride, glucose, and such, can also be added into the injection. Further, an analgesic, such as benzalkonium chloride, or procaine hydrochloride can also be added.

Tablets for oral administration can be prepared by mixing the compound that is the effective ingredient with an excipient, a disintegrator, a binding agent, a lubricant, and such, and compressing and molding it. As an excipient, lactose, starch, mannitol, and such, are generally used. As a disintegrator, calcium carbonate, carboxymethyl cellulose calcium salt, etc. are used in general. As a binding agent, gum arabic, carboxymethyl cellulose, or polyvinylpyrrolidone is used. As a lubricant, talc, magnesium stearate, and such, are well known.

The tablets comprising the pharmaceutical composition of the present invention can be coated for masking and as an enteric-coated agent using well-known methods. As a coating agent, ethylcellulose, polyoxyethyl glycol, and such, can be used.

The effective ingredient content in the pharmaceutical composition of the current invention is determined based on the administration form and the amount required. For example, in the case of oral administration, the generally acceptable amount effective for a day may be about 0.1 to 1000 mg of anti-MK protein antibody, and more generally, about 50 to 200 mg.

The present invention also provides a method for screening a compound for the prevention or treatment of restenosis. Because the preventive or therapeutic effect on restenosis is achieved through inhibiting the function of MK, effective compounds can be screened by using the MK inhibiting function as an index. Some already established methods can be used for screening candidate compounds that inhibit the synthesis of MK. For example, there are numerous cell lines in which the synthesis of MK is active. The level of MK produced by these cells can be measured by, for example, radioimmunoprecipitation, western blot technique, RIA, or ELISA. The MK level is decreased by treating MK producing cells with an effective candidate compound.

MK activity can be directly analyzed. As described previously, cell lines having increased MK levels are available. These cells are also characterized by some abnormal behavior, such as colony formation in soft agar. Using these cells, the increase of endothelial cell proliferation can be measured. This is a useful in vitro model for angiogenesis in vivo. The behavior of cells changes when treated with an effective candidate compound, and thus, can be used to identify useful compounds. The above-mentioned assay is useful as a standard model for angioendothelial cell proliferation. The in vivo efficiency and safety of selected candidate compounds can be tested using an animal model system.

BEST MODE FOR CARRYING OUT THE INVENTION

Figure 1:
FIG. 1 shows the time course of mRNA expression in blood vessel tissues of the experimental restenosis model in rats, detected by RT-PCR. (a) indicates the time course of mRNA expression for MK, (b) for Pleiotrophin (PTN), (c) for Syndecan-1, Syndecan-3 and Syndecan-4, (d) for RPTP-β, and (e) for GAPDH, respectively.
Figure 1:
Figure 1:
Figure 1:
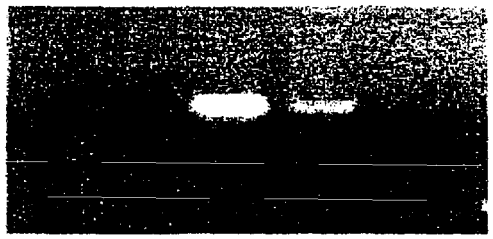
Figure 1:
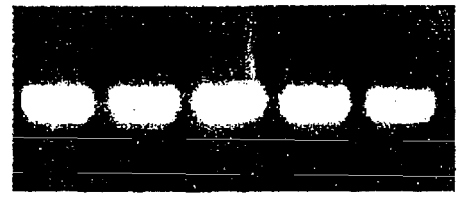

The present invention is illustrated in detail below with reference to Examples, but it is not to be construed as being limited thereto.

Example 1

Preparation of Restenosis Model

Rat carotid artery balloon injury model was prepared as follows. Fifteen to twenty week-old male Wistar rats (body weight: 350 to 400 g) were anesthetized by administering 50 mg/kg of Nembutal. Limbs of the rats were fixed on a fixed plate. The column was incised along the median line to expose the external carotid artery. The external carotid artery at the region where the external carotid artery and the internal carotid artery branch out from the common carotid artery was rounded with two pieces of thread with an appropriate interval. The distal region was ligated, and proximal region was readied for ligation. The small part of the external carotid artery between the two pieces of thread was incised. A 2F Fogarty catheter was inserted through this incision into the common carotid artery, and further to its origin. A balloon was inflated with physiological saline at the origin of the common carotid artery until some resistance was created, and pulled back to the branched carotid artery region while rotating slowly. After the balloon was contracted, the catheter was again inserted to the origin, and the balloon was inflated again and pulled back. This procedure was repeated again. This treatment peeled off the endothelium of blood vessels and damaged tunica media of smooth muscle to create intimal thickening. The catheter was pulled out, and at the same time, the thread at the proximal region was ligated. The operated region was sutured to complete the preparation of rat carotid artery balloon injury model (restenosis model). After the rats recovered from anesthesia, they were housed in separate cages.

Example 2

Analysis of Intimal Thickening and MK Expression

Using the restenosis model, the relationship between intimal thickening and MK expression was analyzed by 1) PCR, 2) western blot technique, and 3) histomorphological observation.

(1) Detection of MK Expression by PCR

Three normal rats (control group), and three each for every restenosis model group (3 hours, 3 days, 7 days, and 14 days after the catheter injury) were prepared.

(a) Detection of mRNA for Each Protein in Blood Vessel Tissues by RT-PCRSPO

The expression amounts of mRNA for MK, PTN, Syndecan-1, Syndecan-3, Syndecan-4, RPTP-β, and GAPDH (the internal standard) in blood vessel tissues from the control and restenosis groups (3 hours, 3 days, 7 days, and 14 days after the injury) were detected by RT-PCR. From each tissue, mRNA was prepared, and RT-PCR was conducted for the mRNA, the starting material. Primers were prepared by selecting the best parts of known regions (Kurabo Ltd.). The nucleotide sequences of the primers used are as follows.

```
MK sense primer
                                          (SEQ ID NO: 1)
5'-gccggatccatgcagcaccgaggcttcttc-3'
(30 mer)

MK antisense primer
                                          (SEQ ID NO: 2)
5'-actagcataatcaggaacatcatagtcctttccttttcctttt-3'
(42 mer)

PTN sense primer
                                          (SEQ ID NO: 3)
5'-actggtgccgagtgcaaacaa-3'
(21 mer)

PTN antisense primer
                                          (SEQ ID NO: 4)
5'-gagtttgccacagggcttgga-3'
(21 mer)

syndecan-1 sense primer
                                          (SEQ ID NO: 5)
5'-ggaggcacttctgtcatcaa-3'
(20 mer)

syndecan-1 antisense primer
                                          (SEQ ID NO: 6)
5'-agcacttccttcctgtccaa-3'
(20 mer)

syndecan-3 sense primer
                                          (SEQ ID NO: 7)
5'-gatgagccagaggtgccagt-3'
(20 mer)

syndecan-3 antisense primer
                                          (SEQ ID NO: 8)
5'-gccacctacgatcacagcta-3'
(20 mer)

syndecan-4 (ryudocan) sense primer
                                          (SEQ ID NO: 9)
5'-gaagacgctgggggccttgag-3'
(21 mer)

syndecan-4 (ryudocan) antisense primer
                                          (SEQ ID NO: 10)
5'-tctgaggggacacggatgcca-3'
(21 mer)

RPTP-β sense primer
                                          (SEQ ID NO: 11)
5'-atcggatcccgttctcaacacatccctgaat-3'
(32 mer)

RPTP-β antisense primer
                                          (SEQ ID NO: 12)
5'-cgtctcgagctaagcatctggagaaaatgtctc-3'
(33 mer)

GAPDH sense primer
                                          (SEQ ID NO: 13)
5'-gaccacagtccatgccatcac-3'
(21 mer)

GAPDH antisense primer
                                          (SEQ ID NO: 14)
5'-gtagccgtattcattgtcatacc-3'
(23 mer)
```

PCR was conducted under the following conditions: heat denaturing was done at 94° C. for 30 sec (1st cycle was 1 min); annealing at 55° C. for 30 sec; and elongation at 72° C. for 30 sec, with 28 cycles for MK, 35 cycles for PTN, 33 cycles for Syndecan-1, Syndecan-3, and Syndecan-4, cycles for RPTP-β, and all cycles described above for GAPDH. FIGS. 1 (a), (b), (c), (d), and (e) show the results of the above-mentioned RT-PCR.

(b) Quantification of MK mRNA by Competitive PCR

Figure 2:
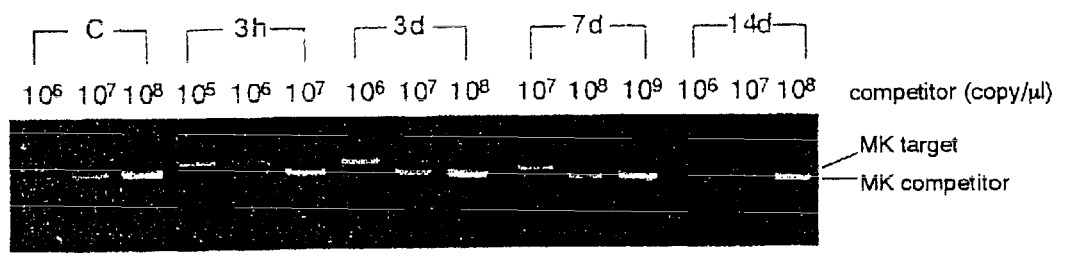
FIG. 2 shows the time course of mRNA expression in blood vessel tissues of the experimental restenosis model in rats, quantitatively detected by the competitive PCR method. GAPDH was used as the internal standard.
Figure 2:
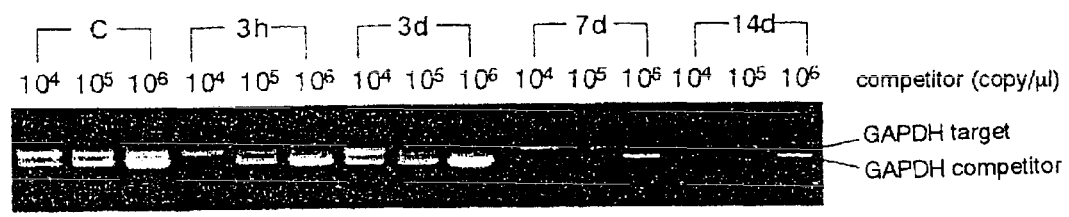

The expression amounts MK and GAPDH mRNA in blood vessel tissues from the control and restenosis model groups (3 hours, 3 days, 7 days, and 14 days after the injury) were quantified by competitive PCR (FIG. 2 a and b). The concentrations of target and competitor bands were judged visually. The bands of the target and the competitor (the upper and lower) with approximately the same concentration were arranged in the middle. For MK, the copy number of the competitors in the control group (C) was $10^7$, same as that of the target, was decreased to be the same as $10^6$, 3 hours after the injury, and was increased to be the same as $10^8$, 7 days after the injury. It was confirmed that MK mRNA was expressed about 10 times more than the control 7 days after the injury. In contrast, the amounts of GADPH expression were the same as $10^5$ for the control group (C), and 3 hour, 3 day, 7 day, 14 day post-injury groups, showing a constant amount of mRNA for all samples used.

(2) Western Blot Analysis

Two normal rats (control group), and two rats each for every restenosis model group (3 hours, 3 days, 7 days, and 14 days after the catheter injury) were prepared.

Figure 3:
FIG. 3 shows the time course of the expression amount of MK protein in blood vessel tissues of the experimental restenosis model rats, analyzed by the western blotting method.

The expression amounts of MK proteins in blood vessel tissues were analyzed by the western blot technique (FIG. 3). FIG. 3 shows that the expression amount of MK protein 3 hours after the preparation of restenosis model did not differ from that for the control group, however, 7 days after the injury, the MK expression amount was maximum, and 14 days after the injury the expression amount of MK protein was decreased, but was still higher than the control group.

(3) Histomorphological Analysis

Three normal rats (control group), and rats for every restenosis model group (three rats for the 3 days post-catheter injury model group, four rats for the 7 days post-catheter injury model group, and three rats for the 14 days post-catheter injury model group) were prepared.

(a) Hematoxylin-Eosin Staining

Figure 4:
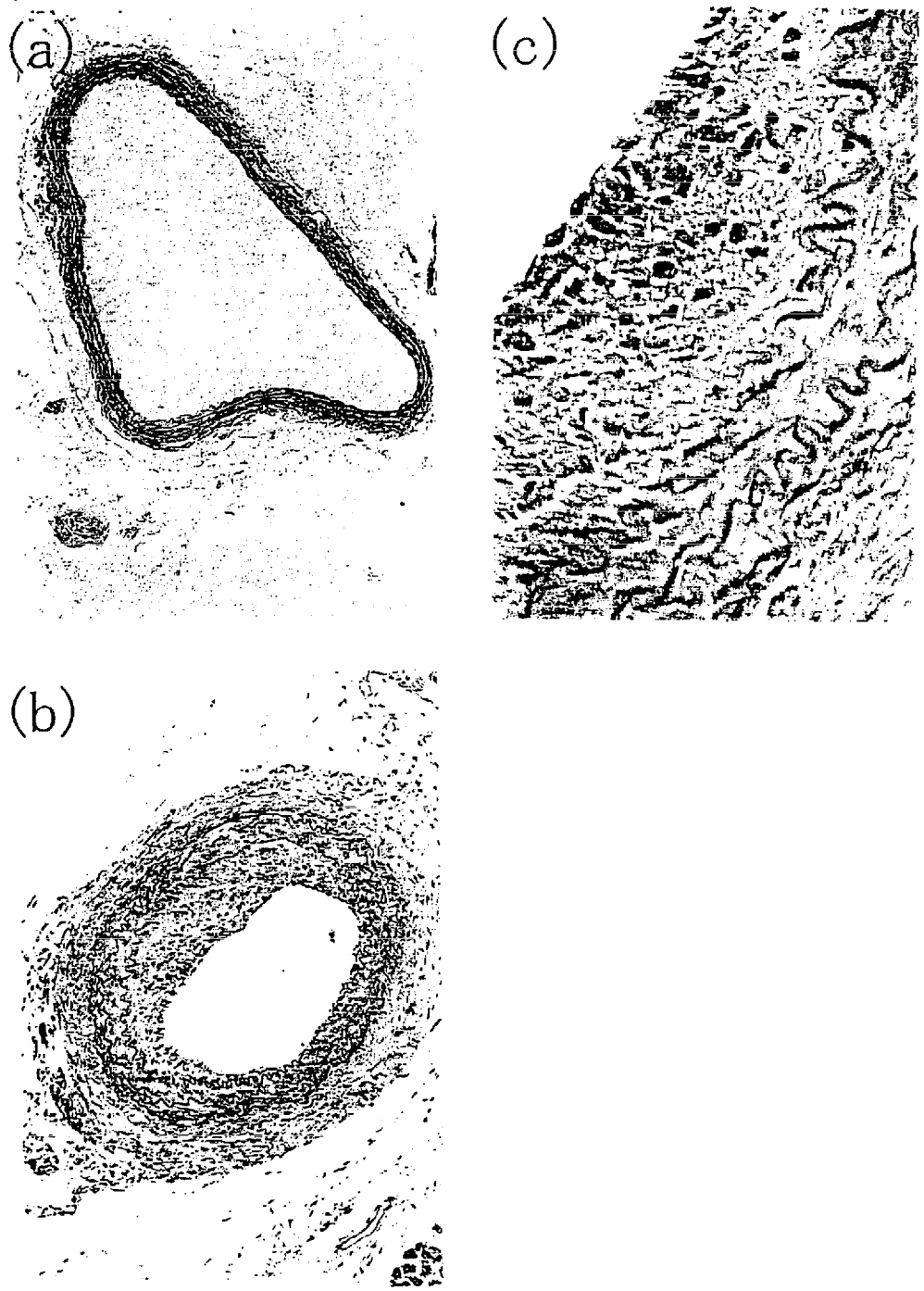
FIG. 4 shows a paraffin section of blood vessel tissues stained by hematoxylin-eosin (H. E) 14 days after catheter injury. H. E staining for the control group 14 days after the beginning of the experiment (a), for the group 14 days after restenosis model preparation (b), and the magnified figure of FIG. 4-a (c) are shown.

The sections of the blood vessel tissues were prepared using 4% paraformaldehyde (Wako Pure Chemical Industries Ltd. fixative. After the sections were embedded in paraffin using an automatic embedding machine, a 5 μm slice was prepared and stained with hematoxylin-eosin (hereafter, referred as H.E staining) (FIG. 4 a, b, and c). FIG. 4 a shows the H.E staining for the control group, FIG. 4 b the H.E staining 14 days after catheter injury, and FIG. 4 c a magnified figure of FIG. 4 a. FIG. 4 clearly shows that no intimal thickening was observed in the control group, but obvious thickening was found in the restenosis model 14 days after catheter injury.

(b) Immunohistochemistry

Figure 5:
FIG. 5 shows the immunohistochemical staining of a paraffin section of blood vessel tissues 14 days after catheter injury in rats, using the anti-MK polyclonal antibody, and the anti-rabbit IgG antibody as the secondary antibody (Jackson laboratory).

The sections of blood vessel tissues 14 days after catheter injury were immunohistochemically stained using the anti-MK polyclonal antibody, and the anti-rabbit IgG antibody (Jackson Laboratory) as a secondary antibody (FIG. 5). A significant MK protein expression was seen in the neointima.

Example 3

The Effects of MK on Neointima Formation in MK Knockout Mice

In order to examine the relationship between restenosis and MK expression under conditions closer to in vivo, the effect of MK on neointima formation was tested using MK gene knockout mice. MK was prepared by the method described in Examples of JP-A No. Hei 9-95454.

The homogeneous knockout mice (129/Sv line, 10 to 12 week-old male mice, bodyweight: 25 to 30 g) were prepared by destroying partial regions of exons 2 and 3 in the MK gene (Gene Cells, 1998 Dec., 3(12), 811-822).

Four groups, the wild mice (129/Sv line, 10 to 12 week-old male mice, body weight: 25 to 30 g, 10 individuals), MK knockout mice (10 individuals), MK knockout mice transplanted with a physiological saline injection pump (10 individuals), and MK knockout mice transplanted with a MK injection pump (10 individuals), were prepared.

Nembutal (50 mg/kg) was intraperitoneally administered to anesthetize the mice of each group. The neointima formation model was prepared by ligating the branched common carotid region. A complete occlusion due to thrombi does not easily occur probably because the mice tend to have relatively higher blood pressure, and stimuli from the loading pressure forms neointima (Arterioscler Thromb Vasc Biol. 1997, 17: 2238-2244).

Pathological analysis of the neointima revealed that the neointima in the wild mice was remarkably increased compared with that in the MK knockout mice. These results and the results of Example 1 imply that MK might be involved in neointima formation.

Neointima formation models were constructed by preparing two groups of MK knockout mice, those given MK and those given physiological saline (control group) (10 mice in each group). A pump injected with 100 μl of 0.8 mg/ml MK (Micro-Osmotic Pump "alet-MODEL 10070": alza; 0.5 μl/hr., effective for 7 days), or a pump injected with physiological saline was subcutaneously transplanted under abdominal skin of mice, replacing with a new pump 7 days after the first transplantation, and kept until 14 days after the first transplantation when the mice were sacrificed to analyze the state of neointima formation.

Blood vessels were fixed in 4% paraformaldehyde (Wako Pure Chemical Laboratories Ltd.). After they were embedded in paraffin using an automatic embedding machine, 5 μm slices were prepared and stained with H.E for observation. Neointima was excessively formed in the MK administered group, compared with the control group. The results of the experiment in vivo using the knockout mice indirectly proved that MK is involved in the restenosis after a vasodilation operation.

INDUSTRIAL APPLICABILITY

The administration of the pharmaceutical composition of the present invention effectively prevents the stenotic symptoms of blood vessels attributed to arteriosclerosis or restenosis after PTCA surgery. In addition, the pharmaceutical composition of this invention is therapeutically useful for alleviating progressed stenotic symptoms of blood vessels.

We claim:

1. A method for the treatment of angiostenosis caused by restenosis following percutaneous transluminal coronary angioplasty (PTCA), wherein said method comprises administering to the blood vessel or intima of a patient subjected to PTCA, an amount of a midkine (MK) inhibitory compound effective to suppress neointima formation, thereby treating the restenosis and wherein the MK inhibitory compound is an anti-MK antibody or antibody fragment that binds MK protein or an oligonucleotide that binds to mRNA encoding MK.

2. The method according to claim 1, wherein the MK inhibitory compound is an antibody or antibody fragment that binds to MK protein.

3. The method according to claim 2, wherein the antibody is a monoclonal antibody that binds to MK.

4. The method according to claim 2, wherein the antibody fragment is a single chain variable region fragment (scFv) that binds to MK.

5. The method according to claim 2, comprising administering the antibody or antibody fragment by intravenous infusion.

6. The method according to claim 1, wherein the MK inhibitory compound is an oligonucleotide that binds to mRNA encoding MK to thereby inhibit expression of MK and suppress neointima formation.

7. The method according to claim 6, wherein the oligonucleotide binds to a sequence of MK encoding MK comprising nucleotides 1 to 14 of SEQ ID NO:15.

8. The method according to claim 6, wherein the oligonucleotide binds to a sequence of MK encoding MK comprising nucleotides 2 to 16 of SEQ ID NO:15.

9. The method according to claim 6, wherein the oligonucleotide binds to a sequence of MK encoding MK comprising nucleotides 3 to 17 of SEQ ID NO:15.

* * * * *